(12) United States Patent
Sato et al.

(10) Patent No.: US 7,951,844 B2
(45) Date of Patent: May 31, 2011

(54) TRANQUILIZER AND FUNCTIONAL FOOD

(75) Inventors: Toshiro Sato, Hukuroi (JP); Shuichi Kamo, Hukuroi (JP); Rumi Kawahara, Hukuroi (JP)

(73) Assignee: J-Oil Mills, Inc. (JP)

( * ) Notice: Subject to any disclaimer, the term of this patent is extended or adjusted under 35 U.S.C. 154(b) by 0 days.

(21) Appl. No.: 12/529,347

(22) PCT Filed: Mar. 27, 2008

(86) PCT No.: PCT/JP2008/000770
§ 371 (c)(1),
(2), (4) Date: Sep. 1, 2009

(87) PCT Pub. No.: WO2008/126367
PCT Pub. Date: Oct. 23, 2008

(65) Prior Publication Data
US 2010/0099918 A1    Apr. 22, 2010

(30) Foreign Application Priority Data

Apr. 5, 2007   (JP) ................................ 2007-099323

(51) Int. Cl.
*A61K 31/12* (2006.01)
*C07C 49/303* (2006.01)

(52) U.S. Cl. ...................................... 514/690; 568/328

(58) Field of Classification Search .................. 568/328; 514/690
See application file for complete search history.

(56) References Cited

U.S. PATENT DOCUMENTS

| | | | |
|---|---|---|---|
| 2002/0025983 A1 | 2/2002 | Horrobin |
| 2002/0146463 A1 | 10/2002 | Clayton |
| 2005/0107472 A1 | 5/2005 | Wischik |
| 2006/0058398 A1 | 3/2006 | Kamei |

FOREIGN PATENT DOCUMENTS

| | | |
|---|---|---|
| DE | 20 2007 000949 | 4/2007 |
| JP | 2003-226639 | 8/2003 |
| JP | 2004-501937 | 1/2004 |
| JP | 2004-515508 | 5/2004 |
| JP | 2004-534854 | 11/2004 |
| WO | WO 91/11117 | 8/1991 |
| WO | WO 96/24345 | 8/1996 |
| WO | WO 98/08522 | 3/1998 |
| WO | WO 02/01969 | 1/2002 |
| WO | WO 2006/005185 | 1/2006 |
| WO | WO 02/47493 | 3/2006 |

OTHER PUBLICATIONS

Cocchetto, DM et al. "Behavioral Pertubations in the Vitamin-K Deficient Rat". Physiology & Behavior, (1985) 34 p. 727-734.
Sumi, Hiroyuki et al. "Sakekasurui, Tokuni Shochu Joryyukasu o Genro to Shita Nattokinase Oyobi Vitamin K2 (Menaquinone-7) no Hakko Seisan", Journal of the Brewing Society of Japan, (2004) 99 (12), pp. 867-872.
Shirakawa, Hitoshi et al. "Sanka Stress ni yoru Shinkei Saibo no Apoptosis o Sogai suru Vitamin K no Sayo", Vitamins, (2004) 78(3), pp. 147-150.
JuneJA, L.R. et al.: "L-Theanine—A Unique Amino Acid of Green Tea and its Relaxation Effect in Humans", Trends in Food Science and Technology, Elsevier Science Publishers, GB, vol. 10, No. 12, Jan. 1, 1999, pp. 199-204.
Miyamoto et.al,, Characterization of the anxiolytic-like effects of fluvoxamine, milnacipran and risperidone in mice using the conditioned fear stress paradigm, Eur. J. Pharmacol. 504, p. 97-103, 2004.
Inoue et al., Serotonergic activation reduces defensive freezing in the conditioned fear paradigm, Pharmacol. Biochem. and Behavior 1996, 53, p. 825-831.
Stephen M. Stahl, Stahl's Essential Psychopharmacology: The Prescriber's The Prescriber's Guide, Third edition (2009), pp. 83, 139, 215, 341, 475.

*Primary Examiner* — Sikarl Witherspoon
(74) *Attorney, Agent, or Firm* — Galbreath Law Offices, P.C.; John A. Galbreath

(57) ABSTRACT

This invention provides a pharmaceutical and functional food which are made of a safe food ingredient or nutrient which has been used for a long period of time, and which have tranquilizing effect such as anti-anxiety effect, anti-depression effect, and anti-stress effect. The tranquilizer of the invention contains vitamin K as an active ingredient. Vitamin K is preferably menaquinone-4 and/or menaquinone-7. This invention also provides a supplement, health food or functional food for tranquilizing purpose that contains vitamin K as an active ingredient.

2 Claims, 2 Drawing Sheets

TRANQUILIZER AND FUNCTIONAL FOOD

FIELD OF THE INVENTION

This invention relates to a tranquilizer and a functional food containing the same. More specifically, this invention relates to a safe tranquilizer of food origin and a functional food containing the same.

BACKGROUND ART

Increase in mental diseases, in particular depression, anxiety, autonomic imbalance and the like caused by excessive stress due to mental or physical pain has become a serious problem. Against such backdrop, many anti-depressants and anti-anxiety agents containing a chemical substance as active ingredient have been developed and used. Meanwhile, it is also known that conventional pharmaceutical drugs have problems of side effects, dependence and the like.

A safe ingredient originating from foods and having the function described above is desirable. Examples of foods and food ingredients that are known to have anti-depression effect and anti-anxiety effect include GABA, ginseng, St. Jone's wort, and Apocynum venetum extract. Examples of foods and food ingredients that are known to have anti-stress effect include theanine, soy bean peptide, cacao polyphenol, a matsutake mushroom and *Grifola frondosa* (Non-Patent Document 1). However, their effects are all moderate.

Non-Patent Document 1: Development and Prospects of Anti-stress Foods, Supervised by Hidehiko Yokogoshi, CMC Publishing CO., LTD (2006)

DISCLOSURE OF INVENTION

While a safe food ingredient or nutrient which is widely used as food and which exerts tranquilizing effect such as anti-anxiety effect, anti-depression effect, and anti-stress effect would be preferable, such food ingredients have not been known yet. Under such circumstances, an object of the present invention is to provide a substance exerting significant tranquilizing effect which is originating from a safer food ingredient which has been widely used as food for a long period time.

The inventors found that vitamin K1 and vitamin K2 taken from foods are converted into menaquinone-4 (MK-4) in a body tissue. The inventors attempted to clarify the function of vitamin K in the brain based on the findings that the MK-4 concentration is particularly high in the brain. Through such studies, the inventors found that vitamin K has tranquilizing effects such as anti-anxiety, anti-depression and anti-stress and achieved the present invention. In other words, this invention provides a tranquilizer that contains vitamin K.

In the present specification, the term "tranquilizer" is used as a superordinate of anti-anxiety agent, anti-depressant, anti-stress agent and the like.

The currently known function of the vitamin K is limited to suggestion of involvement thereof in the sphingolipid concentration (Carrie, I et. al. (2004) J. Nutr. 134, 167-172) and metabolism of sulfatide (Denisova, N A & Booth, S L (2005) Nutr. Rev. 63, 111-121), and has not been clarified yet. Accordingly, although involvement of vitamin K in some physiological functions in the brain is suggested, it was not foreseen at all that administration of vitamin K to an animal including a human would cause a tranquilizing effect.

Vitamin K includes vitamin K1 produced by plants, vitamin K2 produced by microorganisms, and vitamin K3 which is a synthetic compound. Vitamin K2 is further classified into MK-4 to MK-15 depending on the length of isoprenoid side chain. Since vitamin K is converted into MK-4 in the body as described above, either vitamin K1 or vitamin K2 may be used as vitamin K for a pharmaceutical of the invention. Preferably, vitamin K2 having higher physiological activity shall be used, and more preferably, menaquinone-4 and/or menaquinone-7 shall be used.

Furthermore, this invention provides a supplement, health food, or functional food containing said tranquilizer.

An anti-anxiety agent containing vitamin K as active ingredient according to the present invention provides a tranquilizer highly safe to human body. While the adequate amount of vitamin K that a human requires a day is in a range from 55 to 80 μg (according to Dietary Reference Intake of Japanese, 2005), the tolerable upper intake level of vitamin K has not been set. Based on this fact, it can be said that vitamin K is a safe substance. Accordingly, the tranquilizer of the invention is superior in terms of safety to conventionally known anti-anxiety agents, anti-depressants and anti-stress agents.

The tranquilizer of the invention also has an advantage that the effect lasts for a long period of time, because vitamin K, which is fat soluble, is easier to be accumulated in the body than a conventional anti-anxiety agent, anti-depressant and anti-stress agent.

Furthermore, the tranquilizer of the invention also aims to prevent illness such as depression, since it is extremely easy to be taken daily as a functional food and health food.

DETAILED DESCRIPTION OF THE PREFERRED EMBODIMENTS

Figure 1:
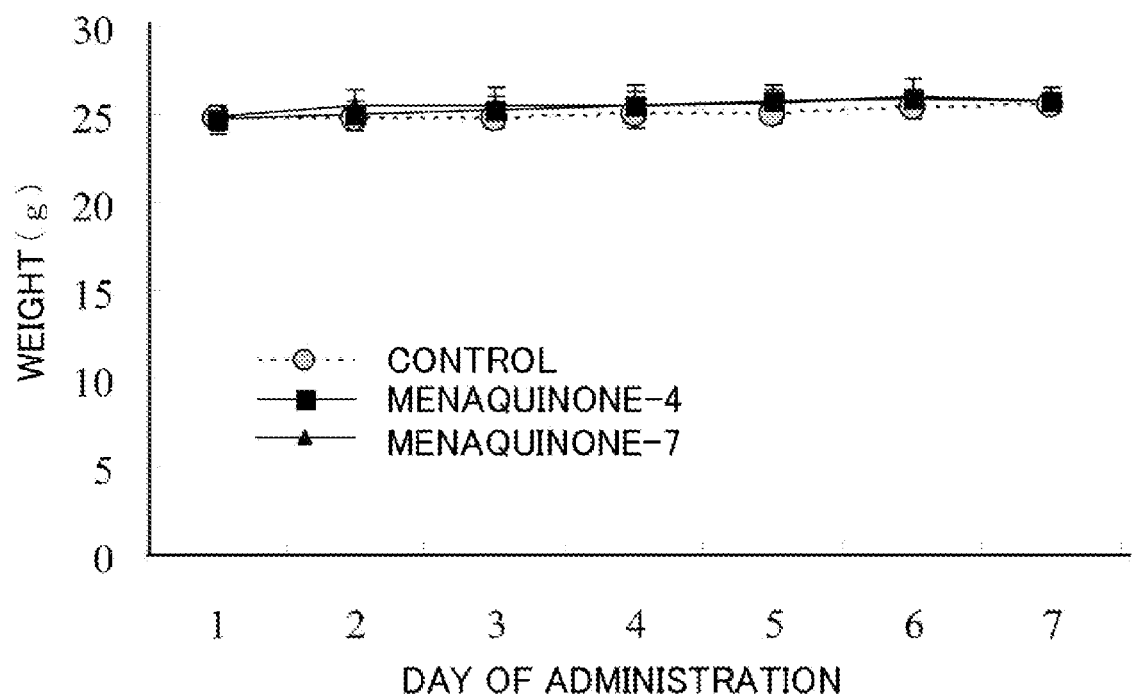
FIG. 1 shows a change in weights of mice in vitamin K groups of the invention and in a control group (medium control group) as comparative example for a week during which the mice took feed. The data is shown as the mean value ±the standard deviation value for 10 mice. As a result of analysis of the values by the Student's t-test in the control group and in the menaquinone-4 group or the menaquinone-7 group, the significant difference was not observed.

One embodiment of a tranquilizer of the invention will now be described in detail. Firstly, vitamin K usable for the tranquilizer of the invention includes vitamins K1 to K3. Vitamin K1 is contained in large quantity in green and yellow vegetables, beans, vegetable oils, sea alga, fishery products and the like. Vitamin K1, which is a fat soluble light yellow oil, is stable to heat, but it is unstable to light. Vitamin K1 may be in a form of oxide.

Vitamin K1 is extracted and refined by a known method (for example, in Japanese Patent Laid-Open No. 5-155803) from Japanese basil, perilla, molokheiya, parsley, garland chrysanthemum, Japanese mustard spinach, spinach, Japanese honeywort, alfalfa, leaf of hazel, leaf of chestnut, young stem of barley, young stem of oat, cabbage, broccoli, cauliflower, tomato, vegetable oils (ex. soy bean oil, canola oil, sesame oil, peanut oil, corn oil, safflower oil, sunflower oil, rice bran oil, and olive oil) or the like. Vitamin K1 is also obtained synthetically. Commercially-available vitamin K1 can also be used for the invention without limitation.

Vitamin K2 includes homologs from menaquinone-15 (MK-15) to menaquinone-4 (MK-4) depending on the length of the side chain isoprenoid group attached to the naphthoquinone skeleton. Vitamin K2 is produced by a microorganism and is contained in large quantity in fermented soybeans and dairy products such as cheeses. For example, MK-6 to MK-9 are contained in cheeses and MK-7 is contained in fermented soybeans in large quantities, respectively. Vitamin K2 is also produced by bacteria in the intestinal tract.

Vitamin K2 is produced by fermentation by microorganisms such as *bacillus natto* according to the methods described in, for example, Japanese Patent Laid-Open Nos. 08-073396, 11-92414, 10-295393, and 2001-136959. Commercially-available vitamin K2 can also be used for the invention without limitation.

It is known that, the side chains of vitamin K1 or K2 taken from foods are detached in the body, whereby vitamin K1 or K2 is converted into a geranyl group, and further converted into MK-4. Accordingly, MK-4 is thought to have a direct effect different from γ carboxylation of a vitamin K-dependent protein, and thus MK-4 is also called active vitamin K. It is also known that MK-4 increases in the brain more remarkably when MK-7 originating from fermented soybeans is taken than when MK-4 is taken directly (Rumi Ozaki et al., (2006), Vitamins, 80, 203).

The vitamin K3 is a synthetic compound. Side effects are concerned when vitamin K3 is taken in large quantity. Accordingly, vitamin K1 extracted and refined from vegetables and vitamin K2 extracted from substances fermented by using *Bacillus natto* or the like are preferable because they are safer based on the eating experience. Vitamin K2 is more preferable, since it can be easily produced at a lower cost. Independent or combined use of menaquinone-4 (MK-4) and menaquinone-7 (MK-7) experienced as food material is particularly preferable.

On top of vitamin K as the essential ingredient, one or more food ingredients or herbs of which anti-depression effect and anti-stress effect have been conventionally known may further be added to the tranquilizer of the invention.

On top of vitamin K as the essential ingredient and a food ingredient and a herb substance having appropriate anti-depression effect and anti-stress effect, pharmacologically available medium, excipient, aid and the like may further be added to the tranquilizer of the invention, as long as they do not inhibit the advantageous effect of the invention.

Specific examples of said media include: carriers or excipients such as lactose, sucrose, fructose, glucose, glucose hydrate, white soft sugar, purified sucrose, erythritol, xylitol, sorbitol, mannitol, palatinose, reduced palatinose, powdered reduced maltose, starch syrup, carmellose, dextrin, sweet corn starch, gelatinized starch, partially gelatinized starch, potato starch, corn starch, hydroxypropyl starch, amino acid, kaolin, silicic anhydride, silicic acid, aluminum silicate, sodium bicarbonate, calcium phosphate, dicalcium hydrogen phosphate, calcium carbonate, magnesium oxide, an aluminium hydroxide, fatty acid excluding essential fatty acids or salt thereof, fatty acid monoglyceride and fatty acid diglyceride, alcohol, vegetable oil, olive oil, soy bean oil, corn oil, fat oil, oils and fats, viscous paraffin, propylene glycol, ethylene glycol, polyethylene glycol, and glycerin; binders such as crystalline cellulose, crystalline cellulose carmellose sodium, methyl cellulose, hydroxypropyl cellulose, low-substituted hydroxypropyl cellulose, hydroxypropyl methyl cellulose, hydroxypropyl methyl cellulose phthalate, hydroxypropyl methyl cellulose acetate succinate, carmellose sodium, ethyl cellulose, carboxymethyl ethyl cellulose, hydroxyethyl cellulose, wheat starch, rice starch, sweet corn starch, potato starch, gelatinized starch, partially gelatinized starch, hydroxypropyl starch, dextrin, pullulan, polyvinyl pyrrolidone, amino alkyl methacrylate co-polymer E, amino alkyl methacrylate co-polymer RS, methacrylic acid co-polymer L, methacrylic acid co-polymer, polyvinyl acetal diethylamino acetate, polyvinyl alcohol, gum arabic, powdered acacia, agar, gelatine, white shellac, tragacanth and macrogol; lubricating agents such as wheat starch, rice starch, sweet corn starch, synthetic aluminum silicate, dried aluminum hydroxide gel, magnesium aluminometasilicate, calcium hydrogen phosphate, dibasic calcium phosphate anhydrous, wax, hydrogenated vegetable oil, polyethylene glycol, light anhydrous silicic acid, synthetic aluminum silicate, stearic acid, macrogol, talc, magnesium stearate, calcium atearate, hydrous silicon dioxide and sucrose fatty acid ester; lubricant; disintegrating agents such as crystalline cellulose, methyl cellulose low-substituted hydroxypropyl cellulose, carmellose, carmellose calcium, carmellose sodium, croscarmellose sodium, wheat starch, rice starch, sweet corn starch, potato starch, partially gelatinized starch, hydroxypropyl starch, carboxymethyl starch sodium and tragacanth; surfactants such as soybean lecithin, sucrose fatty acid ester, stearic acid polyoxyl, polyoxyethylene hydrogenated castor oil, polyoxyethylene polyoxypropyrene glycol, sorbitan sesquioleate, sorbitan trioleate, sorbitan monostearate, sorbitan monopalmitate, sorbitan monolaurate, polysorbate, glyceryl monostearate, sodium lauryl sulfate and lauromacrogol; an emulsifier; solubilizing agents such as disodium phosphate; sorbefacient; pH regulator such as hydrochloric acid, citric acid, sodium citrate, acetic acid, tartaric acid, sodium hydroxide, potassium hydroxide, sodium hydrogen carbonate, sodium carbonate, and lactic acid; brightening agents such as natural resin; stabilizer; antioxidant; preservative; wetting agent; coloring agent; fragrance; and soothing agent.

The content of vitamin K in the tranquilizer of the invention varies depending on the intake amount of the composition. The content may be usually within a range from 0.0001 to 100% by weight, and is preferably 0.001 to 90% by weight, more preferably 0.01 to 70% by weight, and further preferably 1 to 50% by weight. In the case where the vitamin K content is no more than 0.0001% by weight, the quantity necessary for obtaining anti-anxiety, anti-depression and/or anti-stress effect may not be taken.

The tranquilizer of the invention is processed into a form of solution, powder, granule, tablet, capsule, syrup or the like for use as pharmaceutical drug, supplement, functional food or health food. A preferable form is tablet or capsule, since vitamin K is soluble in fat.

The tranquilizer of the invention may be directly added to a raw material when the material is processed into a general processed food such as bread, boiled rice, soup, side dish, cake and candy.

The intake methods of the tranquilizer of the invention when used as pharmaceutical are not particularly limited. For example, they include oral ingestion, transdermal administration, infusion administration, and injection (intramuscular, intraperitoneal, subcutaneous or intravenous). Preferably, a tablet or capsule shall be orally ingested, since it gives less burden to a patient.

The applications of the tranquilizer of the invention include depression, anxiety, neurosis, phobic anxiety disorder, anthropophobia, obsessive-compulsive disorder, panic disorder, posttraumatic stress disorder (PTSD), acute stress disorder, autonomic imbalance, delusional state, hallucination, mania, epilepsy, a fatigue, trepidation, convulsion, sweat, heartbeat, tachycardia, sharp pain, chest pain, headache, enuresis and insomnia arising from these symptoms.

The dosage regimen of the tranquilizer of the invention as pharmaceutical can be determined taking into consideration the symptom and weight of the patient, administration interval, and various factors affecting other clinical effects. Typically, a vitamin K intake amount for a male adult per day may be normally in a range from 10 μg to 100 mg, and preferably 20 μg to 100 mg. For use in therapeutic purposes, vitamin K can be used in the quantity of 6 mg to 100 mg. When a greater effect is expected, a dosage up to 1,800 mg can be used for male adult weighing 60 kg.

In the case where the tranquilizer of the invention is used for a supplement, functional food, health food or general food, the intake amount of vitamin K for a male adult per day is preferably 10 μg to 45 mg, and more preferably 50 μg to 45 mg with safety being taken into consideration.

The tranquilizer of the invention may be used as pharmaceutical or functional food having anti-anxiety, anti-depression and/or anti-stress effects not only for human but also for mammals such as domestic animal and pets. The administration method includes non-oral administration such as injection, and oral intake in the form of functional food and assorted feed.

EXAMPLE

While the present invention will now be explained in more detail with reference to Example, the invention is not limited to Example 1.

Example 1

A stimulus from the outside enters the brain through the sense organs, and is sent to the amygdaloid body and the hippocampus-lateral septum system, where it is judged if the stimulus is beneficial or harmful. (The judgment is referred to as "biological value evaluation"). The information that has been evaluated is stored in the amygdaloid body and the hippocampus. At the same time, biological response occurs, and biological response is visually recognized by an observer as emotional expression. A human and an animal learn (acquire) information on the biological value evaluation they gained through their experiences. When they receive the same stimulus, the stimulus is compared in the amygdaloid body and the hippocampus-lateral septum system. The response that occurs at the time is referred to as "conditioned emotional response". Assume that a rat or mouse is put into a specified box and an electric stimulus it hates is applied to the rat or mouse. Six days later, when the rat or mouse is put in the same box, it causes freezing (akinesia) for a certain period of time though electric stimulation does not apply to it. The akinesia is referred to as "condition-induced akinesia". Currently, an animal model for evaluating anti-anxiety and anti-depression effects is widely used while using decrease of akinesia time as an index. It has been confirmed that akinesia is alleviated by, for example, 7-day oral administration of 30 mg/kg of milnacipran hydrochloride which is a commercially-available anti-depressant.

Whether the tranquilizer of the invention has a similar effect as a commercially-available anti-depressant was examined using said anxiety evaluation system. Specifically, fear-conditioned mice were fed through forced feeding a sample consisting of vitamin K and medium, or a control sample consisting of medium only, respectively, for 7 days. The effect of each sample was examined on the akinesia time of mice.

Preparations

Methyl cellulose (Product name: Metolose (registered trademark), SM-400, hereinafter referred to as "MC") to be used as medium was purchased from Shin-Etsu Chemical Co., Ltd. It was dissolved in an injection solvent (manufactured by Otsuka Pharmaceutical Factory, Inc.) to give a solution of 0.5 w/v %.

Menaquinone-4 and menaquinone-7 as vitamin K to be used as an active ingredient of an anti-anxiety agent of the invention were purchased from Wako Pure Chemical Industries, Ltd. After the given amounts of menaquinone-4 or menaquinone-7 were weighed, they were suspended in 0.5% MC so that a certain concentration is acquired. The control group was fed with only the medium (0.5% MC).

10-week old male mice (C57BL/6NCrlCrlj, SPF grade) were purchased from Charles River Laboratories Japan. After 5-day quarantine period and subsequent 5-day acclimatization, weight measurement and observation of the general condition were conducted once a day. The mice showed no weight change or abnormality in general conditions were subject to the experiment.

The mice were allocated into the groups each consisting of 10 mice according to the random sampling method with use of a computer (CP system for pre-clinical test) so that the mean weights of the individual groups became substantially equal. When the animals were received, they were identified by combined use of the ear punch method and the hair clipping method. After the mice were allocated the groups, they were identified by description on the tails using oil-based ink (in different colors for the individual groups).

The mice were bred in a chamber keeping the following breeding environment: set temperature 23° C. (allowable range: 20 to 26° C.), set humidity 55% (allowable range: 40 to 70%), lighting cycle: 12 hours (to be illuminated from 6:00 a.m. to 6:00 p.m.), number of ventilation: 12 times/hour (fresh air was obtained through sterile filtration). The animals were kept in flat-bed plastic cages (W: 175×D: 245×H: 125 mm) in which autoclaved bedding was installed during the quarantine and acclimatization period and after they were allocated into the groups. Each cage kept 5 mice.

A solid feed (ANG93G, Oriental Yeast Co., Ltd.) was placed in the feeder, and the mice were allowed to freely take the feed. The mice were allowed to freely drink water using a water bottle. The samples were orally administered through forced feeding in accordance specified method, using a disposable syringe made of polypropylene (manufactured by Terumo Corporation, Japan) attached with a disposable feeding needle for mouse (manufactured by Fuchigami kikai Ltd.). The sample was administered while it was stirred with a stirrer. The sample was administered so that the administration quantity of Vitamin K was 30 mg per kg in weight. The administration amount of liquid was calculated based on 10 ml/kg based using the weight on the date of administration.

Test Method

The general conditions and death of a mouse were observed once a day before the administration. The weights were measured once a day before administration. A conditioned-fear measurement system (manufactured by ActiMetrics) was used for measuring electric stimulus and akinesia time. After the mice allocated to the individual groups were placed in the conditioned-fear measurement system, electric stimulus was applied for fear conditioning and the akinesia time was measured simultaneously. Electric stimulus of 0.3 mA for one second in every 15 seconds was applied for 240 seconds. Upon completion of the electric stimulus, the sample was administered to the mice. After 7-day administration, the mice in the control group (0.5% MC) and in the vitamin K-administered groups were placed again in the conditioned-fear measurement system at 2 hours or 2 hours and 1 minute after the final administration, and the akinesia time in 4 minutes was measured under the condition without electric stimulus being applied. The akinesia time was expressed as "% of freezing" for every 60 seconds. Note that the state in which no movement other than skeleton muscle and beard relating to breathing of the mice was judged as "akinesia" and the state where the motion was observed was judged as "active".

Statistical Analysis Method

For the weights, the mean values and the standard deviations were calculated for the individual groups. For the akinesia time, % of freezing was calculated for the entire period from 0 to 240 seconds. Next, the mean values and the standard deviations of "% of freezing" for every 60 seconds and for the entire period from 0 to 240 seconds for the individual groups. The significant difference test was conducted based on the two-group comparative study between the control group and each of the vitamin K groups. The significant difference test of % of freezing for every 60 seconds was conducted based on the two-way analysis of variance. The significant difference test of % of freezing for the entire period from 0 to 240 seconds was conducted based on the test of equality of variance using the F-test between the control group and the test material group. In the case of equal variance, the Student t-test was conducted, and in the case of unequal variance, the Welch test was conducted. The significance probabilities (p value) were shown for all combinations of the comparison. In all test, the level of significance ratio less than 5% was judged as significant. The cases with the level of significance less than 5% (p<0.05) and the cases less than 1% (p<0.01) were shown separately. Note that a commercially-available statistics program (SAS software ReL. 8.2 TS 020, SAS pre-clinical package Version 5.0; SAS Institute Japan Inc.) was used for the significant difference tests as described above. The histogram and the normal distribution were verified based on the obtained results and whereby the test methods were verified. A commercial statistics program (JMP, SAS release 5.1.1; SAS Institute Japan Inc.) was used for verifying the histogram and the normal distribution.

Results

Death or any abnormal general condition was not observed in either the control group or the vitamin K groups. As shown in FIG. 1, the weights remained substantially constant through the administration period in any of the control group, the menaquinone-4 group, and the menaquinone-7 group. No difference was observed among the groups.

Figure 2:
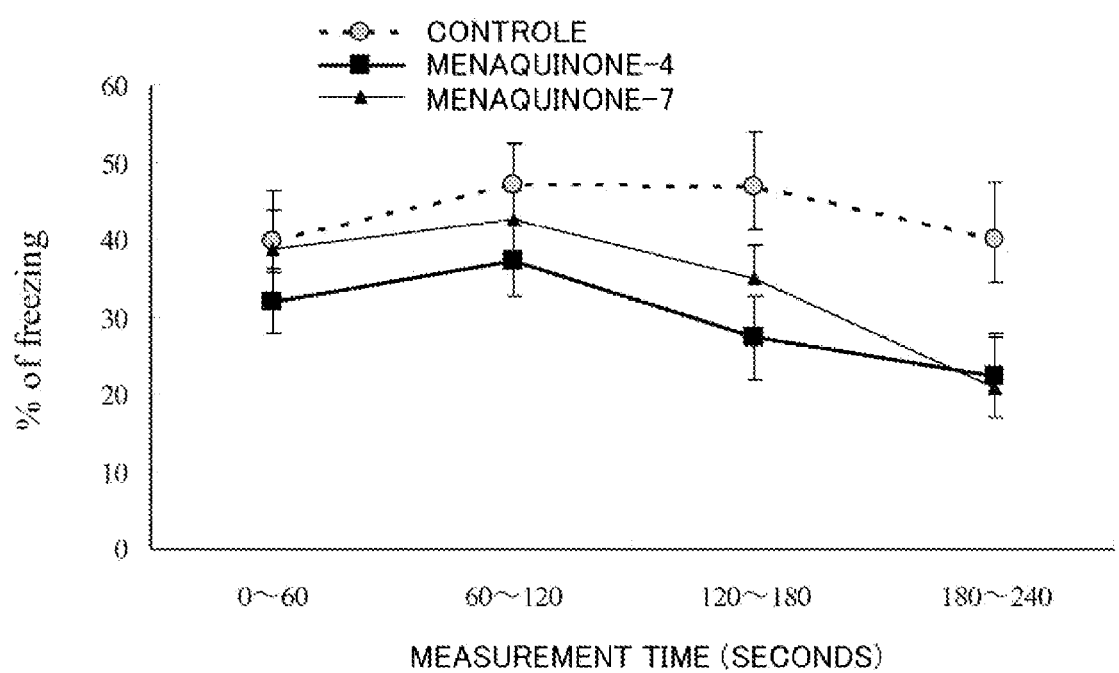
FIG. 2 shows fear condition-induced akinesia time (for every 60 seconds) of the mice in the vitamin K groups of the invention and in the control group as comparative example. The data is shown as the mean value ±the standard deviation value for 10 mice. As a result of two-way analysis of variance, significant decreases in the akinesia time were observed in the menaquinone-4 group and the menaquinone-7 group compared to the control group, with the significance level being $P<0.01$ and $P<0.05$, respectively.

The result of the fear condition-induced akinesia time (for every 60 seconds) is shown in FIG. 2. FIG. 2 shows the ratio (in %) of the time in which no motion was observed during each 60 seconds. A higher ratio in % indicates that the mouse feels more fear, anxiety and stress.

The akinesia time of the control group (medium control group; 0.5% MC group) was 39.85 to 47.03%. On the other hand, the akinesia time of the menaquinone-4 group was 31.99% for the period from 0 to 60 seconds, which was slightly lower than the control group. Subsequently, the akinesia time of the menaquinone-4 group decreased gradually, showing 22.29% for the period from 180 to 240 seconds. As a result of the two-way analysis of variance between the control group and the menaquinone-4 group, significant difference was observed with P<0.01. In the meantime, the akinesia time of the menaquinone-7 group was 38.84% for the period from 0 to 60 seconds, which is substantially the same as that of the control group. Subsequently, the akinesia time of the menaquinone-7 gradually decreased to 20.83% for the period from 180 to 240 seconds, by which significant decrease in akinesia time was observed.

With regard to the vitamin K group, the akinesia time for the menaquinone-4 group was slightly shorter for the period from 0 to 60 seconds, which is the initial period of the measurement, compared to the control group, and the akinesia time for the menaquinone-7 group was substantially equal that of the control group. However, as the measurement time has elapsed, the akinesia time further decreased. This is probably because the exposure of the mice to the place in which fear is conditioned induced anxiety, but subsequently the mouse recognized that it would not receive electric stimulus, and anxiety was alleviated as the time has elapsed. As described above, decrease in fear condition-induced akinesia time, which is an index of anti-anxiety and anti-depression, was observed for vitamin K. It was also found that administration of vitamin K gave tranquilizing effect such as anti-anxiety effect, anti-depression effect and anti-stress effect.

This invention has been so far described in detail with reference to the preferred embodiment. However, those skilled in the art would understand that modification and improvement would be possible within the scope of the invention and within the scope of the spirit of the invention by taking into consideration the disclosure of the present specifications.

The embodiments of the invention include the following.

1. A tranquilizer which contains vitamin K as an active ingredient.

2. The tranquilizer as described in Clause 1, wherein the content of the vitamin K is in a range from 0.0001 to 100% by weight.

3. The tranquilizer as described in Clause 1, wherein the vitamin K is vitamin K2.

4. The tranquilizer as described in Clause 1, wherein the vitamin K is menaquinone-4 and/or menaquinone-7.

5. A supplement, health food or functional food which contains a tranquilizer as described in any one of the above-described clauses.

6. A tranquilizer as described in Clause 1, which is used for a human.

7. A supplement, health food or functional food as described in Clause 5, which is used for a human.

8. A method for curing anxiety, depression and/or stress, comprising administration of a tranquilizer which contains vitamin K as an active ingredient.

9. A method for preventing anxiety, depression and/or stress, comprising administration of a tranquilizer which contains vitamin K as an active ingredient.

10. Use of vitamin K for producing a tranquilizer.

What is claimed is:

1. A method for treating anxiety and/or depression excluding manic depressive psychosis, schizoid and reactive psychosis that are associated with dementia, comprising administration of an anti-anxiety agent and/or anti-depressant which contains vitamin K2 and does not substantially contain essential fatty acids as an active ingredient to a subject in need thereof.

2. The method according to claim 1, wherein the vitamin K2 is menaquinone-4 and/or menaquinone-7.

* * * * *